(12) United States Patent
Abraham et al.

(10) Patent No.: US 10,206,649 B2
(45) Date of Patent: Feb. 19, 2019

(54) DATA TRANSFER ACROSS A ROTATING BOUNDARY OF A COMPUTED TOMOGRAPHY IMAGING APPARATUS

(71) Applicant: Analogic Corporation, Peabody, MA (US)

(72) Inventors: Douglas Abraham, Topsfield, MA (US); Peter Daniel Shippen, Ipswich, MA (US); Carl DeVincent, Lynnfield, MA (US)

(73) Assignee: Analogic Corporation, Peabody, MA (US)

( * ) Notice: Subject to any disclaimer, the term of this patent is extended or adjusted under 35 U.S.C. 154(b) by 363 days.

(21) Appl. No.: 14/982,368

(22) Filed: Dec. 29, 2015

(65) Prior Publication Data

US 2017/0181723 A1    Jun. 29, 2017

(51) Int. Cl.
*A61B 6/03* (2006.01)
*H01Q 1/22* (2006.01)
(Continued)

(52) U.S. Cl.
CPC .............. *A61B 6/56* (2013.01); *A61B 6/035* (2013.01); *A61B 6/032* (2013.01); *H01F 38/18* (2013.01); *H01L 2223/6677* (2013.01); *H01Q 1/2283* (2013.01); *H04B 5/0031* (2013.01); *H04B 5/0037* (2013.01)

(58) Field of Classification Search
CPC .. H05G 1/00; H05G 1/02; H05G 1/08; G01N 2223/304; A61B 6/00; A61B 6/03; A61B 6/032; A61B 6/035; A61B 6/52; A61B 6/56; A61B 6/563; A61B 2560/00; A61B 2560/02; A61B 2560/04; H01L 2223/6661; H01L 2223/6677; G06F 19/32; G06F 1/00; G06F 1/1698; G06F 1/266; G06F 3/00; G06F 3/002; G06F 3/06; G06F 3/0601; H01Q 1/2258; H01Q 1/2266; H01Q 1/2283
See application file for complete search history.

(56) References Cited

U.S. PATENT DOCUMENTS

| | | | | |
|---|---|---|---|---|
| 4,038,662 A | * | 7/1977 | Turner | H01Q 9/065 343/752 |
| 5,592,185 A | * | 1/1997 | Itabashi | H01Q 3/2682 343/767 |

(Continued)

*Primary Examiner* — Anastasia Midkiff
(74) *Attorney, Agent, or Firm* — TraskBritt

(57) ABSTRACT

A receiving antenna for wirelessly receiving data between a stator of a computed tomography (CT) imaging modality and a rotor of the CT imaging modality is provided. The rotor rotates about a rotational axis. The receiving antenna includes a dielectric portion and a conductive portion coupled to the dielectric portion. A second surface of the conductive portion extends between a first end and a second end along a conductive axis that is substantially perpendicular to the rotational axis. The second surface of the conductive portion has a first length at a first length location along a first length axis that is substantially parallel to the conductive axis. The second surface of the conductive portion has a second length at a second length location along a second length axis that is substantially parallel to the conductive axis. The first length is different than the second length.

15 Claims, 7 Drawing Sheets

(51) Int. Cl.
    *A61B 6/00*     (2006.01)
    *H01F 38/18*     (2006.01)
    *H04B 5/00*     (2006.01)

(56) References Cited

U.S. PATENT DOCUMENTS

| | | | | |
|---|---|---|---|---|
| 6,304,219 | B1* | 10/2001 | Rothe | H01Q 1/24 343/700 MS |
| 7,038,631 | B2* | 5/2006 | Jecko | H01Q 9/0421 343/702 |
| 7,248,224 | B2* | 7/2007 | Yuanzhu | H01Q 1/36 343/700 MS |
| 7,598,921 | B2* | 10/2009 | Ge | H01Q 1/2283 343/700 MS |
| 8,077,107 | B2* | 12/2011 | Higaki | H01Q 19/005 343/700 MS |
| 9,590,307 | B2* | 3/2017 | Matsumura | H01Q 9/0407 |
| 2006/0202269 | A1* | 9/2006 | Suzuki | H01L 21/84 257/347 |
| 2007/0171131 | A1* | 7/2007 | Sorvala | H01Q 1/243 343/700 MS |
| 2009/0176450 | A1* | 7/2009 | Chow | H01L 23/48 455/41.1 |
| 2013/0279647 | A1* | 10/2013 | Krupica | G01N 23/046 378/19 |

* cited by examiner

DATA TRANSFER ACROSS A ROTATING BOUNDARY OF A COMPUTED TOMOGRAPHY IMAGING APPARATUS

TECHNICAL FIELD

The present application relates to the transference of information over an airgap separating two members configured for relative rotation. It finds particular application in the context of computed tomography (CT) imaging applications, where at least one of a transmitting antenna or a receiving antenna is located on a rotor and an airgap separating the transmitting antenna from the receiving antenna is small (e.g., 20 mm or less). However, it may also apply to other applications, such as explosive detection machines, radar antennas, etc., for which communication signals are wirelessly transferred.

BACKGROUND

Today, CT and other radiation imaging modalities (e.g., single-photon emission computed tomography (SPECT), mammography, projection radiography, etc.) are useful to provide information, or images, of interior aspects of an object under examination. Generally, the object is exposed to radiation comprising photons (e.g., such as X-rays, gamma rays, etc.), and an image(s) is formed based upon the radiation absorbed and/or attenuated by the interior aspects of the object, or rather an amount of photons that is able to pass through the object. Generally, highly dense aspects of the object absorb and/or attenuate more radiation than less dense aspects, and thus an aspect having a higher density, such as a bone or metal, for example, will be apparent when surrounded by less dense aspects, such as muscle or clothing.

Some radiation imaging modalities, such as CT, are configured to generate volumetric data corresponding to an object under examination. To generate this volumetric data, the CT imaging modality is typically configured to rotate a radiation source and a detector array about the object under examination (e.g., causing the object to be viewed from a plurality of angles). For example, the radiation source and/or the detector array may be mounted to a rotor, also referred to as a rotating gantry, configured for rotation relative to a stator, also referred to as a stationary unit.

Given that the radiation source and the detector array are mounted on the rotor, power and control information (e.g., instructing the radiation source and/or other electronic components how to operate) are typically supplied to the rotor from the stator. Moreover, imaging data (e.g., data generated in response to the detection of radiation by the detector array) and/or status information (e.g., indicative of a status of various components mounted to the rotor) are typically transferred from the rotor to the stator. It may be appreciated that the volume of data transferred, particularly with respect to imaging data, may be quite large. For example, some imaging modalities may require relatively high transfer speeds (e.g., transfers speeds in the gigabit/second range).

Conventionally, slip-ring assemblies have been used to transfer power and/or information (e.g., control information, status information, and/or imaging data) between the stator and the rotor or more generally between a movable unit and a stator (or between two movable units) through the physical contact of two materials (e.g., via a sliding contact). For example, a slip-ring attached to the stator may comprise metal brushes that are configured to physically contact electrically conductive surfaces comprised on a slip-ring attached to the movable unit, allowing power and/or information to be transferred between the stator and the movable unit.

While the use of slip-ring assemblies has proven effective for transferring power and/or information between a stator and a movable unit (e.g., such as a rotor) and/or between two movable units, conventional slip-ring assemblies may generate dust or particles (e.g., as metal brushes wear), may be unreliable (e.g., again as contact surfaces, such as metal brushes, wear), and/or may be noisy (e.g., as surfaces rub against one another), which may cause interference with some procedures (e.g., CT imaging). Other drawbacks of slip-ring assemblies may include cost and complexity of manufacture due to special materials and/or mechanical precision that may be required.

More recently, contactless assemblies have been devised to transfer the data (e.g., or electrical signals corresponding to the data) between the rotor and the stator. While such assemblies overcome many of the aforementioned drawbacks to a slip-ring assembly, the amount of data capable of being transferred via the foregoing contactless assemblies is limited. As radiation imaging modalities continue to develop, data may be required to be transferred at much faster speeds. Further, data may be required to be transferred at a wider range of frequencies than either of the aforementioned assemblies is configured to handle.

BRIEF SUMMARY

Aspects of the present application address the above matters, and others. According to one aspect, the disclosure includes a receiving antenna for wirelessly receiving data between a stator of a computed tomography (CT) imaging modality and a rotor of the CT imaging modality. The rotor is configured to rotate about a rotational axis. The receiving antenna comprises a dielectric portion. The receiving antenna comprises a conductive portion comprising a first surface, which is coupled to the dielectric portion, and a second surface, which is facing away from the dielectric portion. The conductive portion extends between a first end and a second end along a conductive axis that is substantially perpendicular to the rotational axis. The second surface of the conductive portion has a first length at a first length location along a first length axis that is substantially parallel to the conductive axis. The second surface of the conductive portion has a second length at a second length location along a second length axis that is substantially parallel to the conductive axis. The first length is different than the second length.

According to another aspect, the disclosure includes a receiving antenna for wirelessly receiving data between a stator of a computed tomography (CT) imaging modality and a rotor of the CT imaging modality. The rotor is configured to rotate about a rotational axis. The receiving antenna comprises a dielectric portion and a conductive portion comprising a first surface, which is coupled to the dielectric portion, and a second surface, which is facing away from the dielectric portion. The conductive portion extends between a third end and a fourth end along a second conductive axis that is substantially parallel to the rotational axis. The second surface of the conductive portion has a first width at a first width location along a first width axis that is substantially parallel to the second conductive axis. The second surface of the conductive portion has a second width at a second width location along a second width axis that is substantially parallel to the second conductive axis. The first width is different than the second width.

According to another aspect, a computed tomography (CT) imaging modality comprises a stator and a rotor configured to rotate relative to the stator about a rotational axis. The CT imaging modality comprises a receiving antenna coupled to the stator or the rotor for wirelessly receiving data between the stator and the rotor. The receiving antenna comprises a dielectric portion and a conductive portion comprising a first surface, which is coupled to the dielectric portion, and a second surface, which is facing away from the dielectric portion. The conductive portion extends between a first end and a second end along a conductive axis that is substantially perpendicular to the rotational axis. The second surface of the conductive portion has a first length at a first length location along a first length axis that is substantially parallel to the conductive axis. The second surface of the conductive portion has a second length at a second length location along a second length axis that is substantially parallel to the conductive axis. The first length is different than the second length.

Those of ordinary skill in the art will appreciate still other aspects of the present application upon reading and understanding the Detailed Description.

BRIEF DESCRIPTION OF THE DRAWINGS

The application is illustrated, by way of example and not limitation, in the figures of the accompanying drawings, in which like references indicate similar elements and in which.

DETAILED DESCRIPTION

Figure 1:
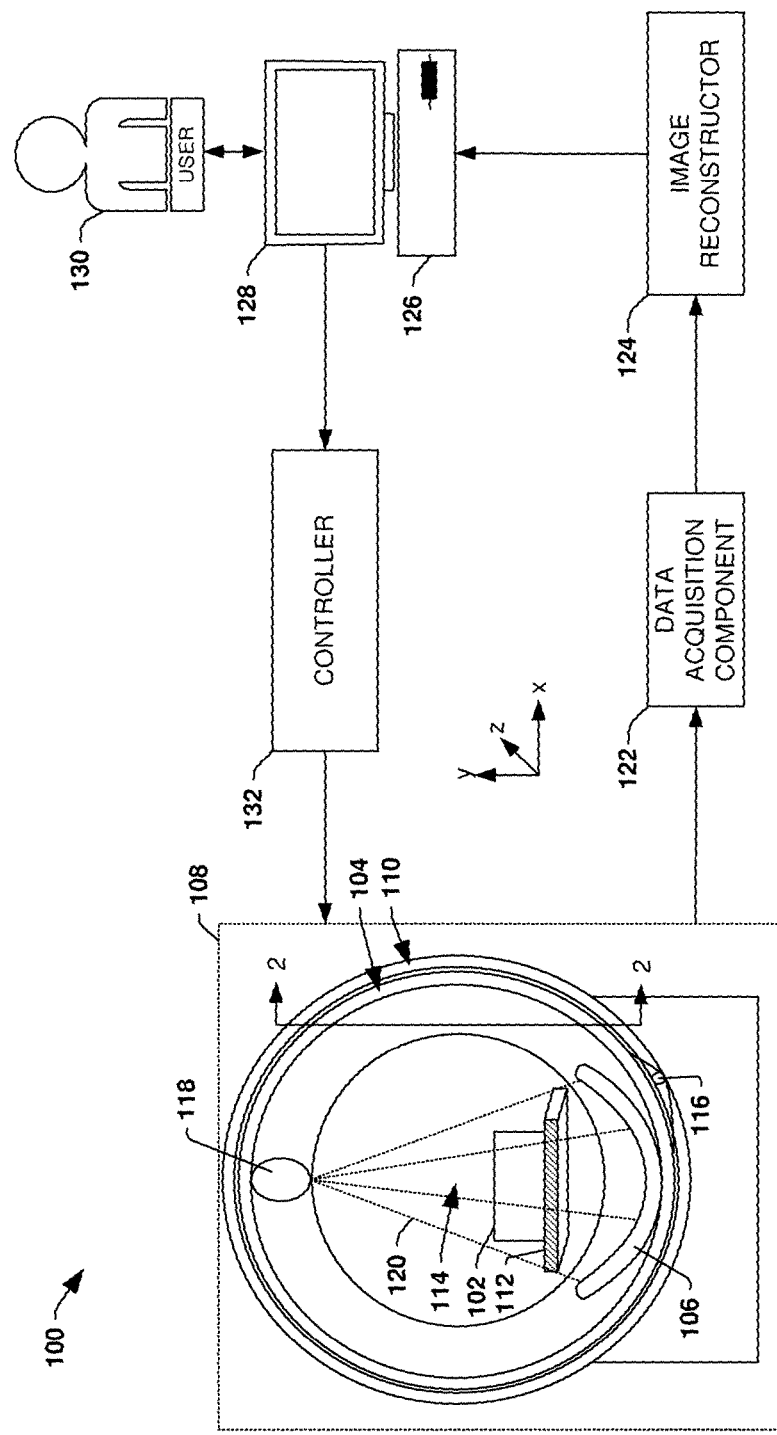
FIG. 1 is a schematic block diagram illustrating an example environment where a data communication system such as described herein may be implemented.

The claimed subject matter is now described with reference to the drawings, wherein like reference numerals are generally used to refer to like elements throughout. In the following description, for purposes of explanation, numerous specific details are set forth in order to provide a thorough understanding of the claimed subject matter. It may be evident, however, that the claimed subject matter may be practiced without these specific details. In other instances, structures and devices are illustrated in block diagram form in order to facilitate describing the claimed subject matter.

The present disclosure relates to a data communication system for transferring data and/or information between two (or more) units. Typically, at least one of the units is movable (e.g., rotating) relative to the other unit. The two units may be separated by an airgap (or gap of some other medium, material, etc.). The data communication system can comprise two or more components. For example, the data communication system can comprise a transmitting antenna that can be coupled to a stator or a rotor. The data communication system can also comprise a receiving antenna that can be coupled to the stator when the transmitting antenna is coupled to the rotor, or to the rotor when the transmitting antenna is coupled to the stator.

The transmitting antenna can transmit data to the receiving antenna by generating an electromagnetic field that corresponds to the data to be transmitted. The transmitting antenna may comprise a pair of transmitting portions that extend annularly about an axis. Ends of the transmitting portions can be separated by a gap. In response to being exposed to the electromagnetic field, the receiving antenna can generate a signal that is proportional to the data being transmitted. Conventionally, in CT applications that employ a contactless data communication system such as described above, the antennas have been designed in accordance with constant impedance ¼ wave non-terminated transmission line technology. The amplitude response of such an antenna is cyclical with respect to frequency. For example, the amplitude response will have a gain of two when the reflecting waves from each end are in phase and a gain of zero when the reflecting waves from each end are out of phase. According to such designs, the receiving antenna has a length that is approximately equal to about half of a wavelength of the signal transmitted by the transmitting antenna thus ensuring sufficient bandwidth for the signal being transmitted. Thus, as a frequency of the signal transmitted by the transmitting increases, the length of the receiving antenna decreases. Such requirements have traditionally limited that frequency of the signal (e.g., and thus the bandwidth of the data communication system), because the length of the receiving antenna must be at least as long as a gap length of the gap separating the transmitting portions to ensure that the receiving antenna continuously receives a signal from the transmission antenna.

Accordingly, as described herein, to accommodate for the gap length of the gap between the ends of the transmitting portions while increasing the frequency of the signals (e.g., and thus the bandwidth of the data communication system), the receiving antenna can have a non-constant length to create a variable impedance antenna. For example, the receiving antenna can have a conductive portion that comprises a first tapered portion and a second tapered portion located at opposing ends of the conductive portion. The signal that is generated within the receiving antenna can partially reflect off of the opposing first tapered portion and then reflect in varying amounts depending on the second conductor geometry from the second tapered portion. This multi-reflection action with certain conductor geometries can be made such that the out of phase wave cancellation can occur at a higher frequency when compared to the normal ¼ wave topology.

It may be appreciated that "noncontact," "contactless," and/or the like is used herein to refer to the ability to transmit information between or among bodies configured for relative movement, and should not be understood to necessarily preclude possible contact between or among such bodies for other purposes, comprising, for example, exchange or communication of data, mechanical drive or support, braking and safety mechanisms, etc.

It may also be appreciated that in the present disclosure, except where otherwise clear from context, "gap" and "airgap" are used more or less interchangeably; although "airgap" may be used herein, as this should be understood to be mere deference to convention, it should be understood that such gaps are not limited to air, it being possible for vacuum, oil, and/or other fluid and/or gas, and/or sliding and/or roller bearings or other such contrivances permitting relative movement to completely or partially fill such spaces. Further, "radiation imaging modality" and/or the like are intended to describe how the imaging modality utilizes radiation to perform an examination.

FIG. 1 is an illustration of an example environment 100 where a data communication system as provided for herein can be useful. More particularly, FIG. 1 illustrates an example computed tomography (CT) imaging modality that can be configured to transmit data regarding an object 102 under examination and generate images therefrom.

It may be appreciated that while a CT imaging modality is described herein, the instant application is not intended to be so limited. That is, to the extent practical, the instant application, including the scope of the claimed subject matter, is intended to be applicable to other apparatuses where an antenna and/or a data communication system comprising such an antenna can be useful. More particularly, the instant application is applicable to other apparatuses where supplying communication information (e.g., control information, status information, imaging information, etc.) to and/or from a movable unit of an apparatus would be useful. Moreover, the example environment 100 merely illustrates an example diagram and is not intended to be interpreted in a limiting manner, such as necessarily specifying the location, inclusion, and/or relative arrangement of the components described herein. For example, a data acquisition component 122 as illustrated in FIG. 1 can be part of a rotor 104 portion of an object examination apparatus 108, or more particularly can be part of a detector array 106.

In the example environment 100, the object examination apparatus 108 is configured to examine one or more objects 102 (e.g., a series of suitcases at an airport, a human patient, etc.). The object examination apparatus 108 can comprise a rotor 104 and a stator 110. During an examination of the object(s) 102, the object(s) 102 can be placed on a support article 112, such as a bed or conveyor belt, that is selectively positioned in an examination region 114 (e.g., a hollow bore in the rotor 104 in which the object(s) 102 is exposed to radiation), and the rotor 104 can be rotated about the object(s) 102 by a rotator 116 (e.g., motor, drive shaft, chain, etc.).

The rotor 104 can surround a portion of the examination region 114 and can comprise one or more radiation sources 118 (e.g., an ionizing X-ray source, gamma-ray source, etc.) and a detector array 106 that is mounted on a substantially diametrically opposite side of the rotor 104 relative to the radiation source(s) 118. During an examination of the object(s) 102, the radiation source(s) 118 emits fan and/or cone shaped radiation 120 configurations into the examination region 114 of the object examination apparatus 108. It may be appreciated that such radiation 120 can be emitted substantially continuously and/or can be emitted intermittently (e.g., a short pulse of radiation 120 is emitted followed by a resting period during which the radiation source(s) 118 is not activated).

As the emitted radiation 120 traverses the object(s) 102, the radiation 120 can be attenuated differently by different aspects of the object(s) 102. Because different aspects attenuate different percentages of the radiation 120, an image(s) can be generated based upon the attenuation, or variations in the number of radiation photons that are detected by the detector array 106. For example, more dense aspects of the object(s) 102, such as a bone or metal plate, can attenuate more of the radiation 120 (e.g., causing fewer photons to be detected by the detector array 106) than less dense aspects, such as skin or clothing.

The detector array 106 is configured to directly convert (e.g., using amorphous selenium and/or other direct conversion materials) and/or indirectly convert (e.g., using a scintillator and photodetectors and/or other indirect conversion materials) detected radiation into analog signals that can be transmitted from the detector array 106 to a data acquisition component 122 configured to convert the analog signals output by the detector array 106 into digital signals and/or to compile signals that were transmitted within a predetermined time interval, or measurement interval, using various techniques (e.g., integration, photon counting, etc.). It can be appreciated that such a measurement interval can be referred to as a "view" and generally reflects signals generated from radiation 120 that was emitted while the radiation source(s) 118 was at a particular angular range relative to the object 102. Based upon the compiled signals, the data acquisition component 122 can generate projection data indicative of the compiled signals, for example.

Information can be transmitted between components physically attached to the rotor 104 (e.g., such as the detector array 106 and/or data acquisition component 122) and components that are not physically attached to the rotor 104 (e.g., such as an image reconstructor 124) through a data communication system. By way of example, the projection space data (at times referred to as imaging data because it is used to reconstruct images of the object) generated by the data acquisition component 122 can be transmitted via the data communication system to an image reconstructor 124 positioned on the stator 110 of the imaging modality. As can be described in more detail below, such a data communication system typically comprises one or more data communication components mounted to the rotor 104 and to the stator 110, where an airgap generally separates a data communication component mounted to the rotor 104 from a data communication component mounted to the stator 110.

The image reconstructor 124 is configured to receive the projection space data that is output by the data acquisition component 122 and to generate image space data from the projection data using a suitable analytical, iterative, and/or other reconstruction technique (e.g., backprojection reconstruction, tomosynthesis reconstruction, iterative reconstruction, etc.). In this way, the data is converted from projection space to image space, a domain that may be more understandable by a user 130 viewing the image(s), for example.

The example environment 100 also comprises a terminal 126, or workstation (e.g., a computer), configured to receive the image(s), which can be displayed on a monitor 128 to the user 130 (e.g., security personnel, medical personnel, etc.). In this way, a user 130 can inspect the image(s) to identify areas of interest within the object(s) 102. The terminal 126 can also be configured to receive user input, which can direct operations of the object examination apparatus 108 (e.g., a speed of a conveyor belt, activation of the radiation source(s) 118, etc.).

In the example environment 100, a controller 132 is operably coupled to the terminal 126. In one example, the controller 132 is configured to receive input from the terminal 126, such as user input, and to generate instructions for the object examination apparatus 108 indicative of operations to be performed. For example, the user 130 can desire to reexamine the object(s) 102 at a different energy level, and the controller 132 can issue a command instructing the support article 112 to reverse direction (e.g., bringing the object(s) 102 back into an examination region 114 of the object examination apparatus 108) and instructing a power supply mounted to the rotor 104 to increase a voltage applied to the radiation source(s) 118 (e.g., causing the radiation 120 output therefrom to have a higher energy).

Figure 2:
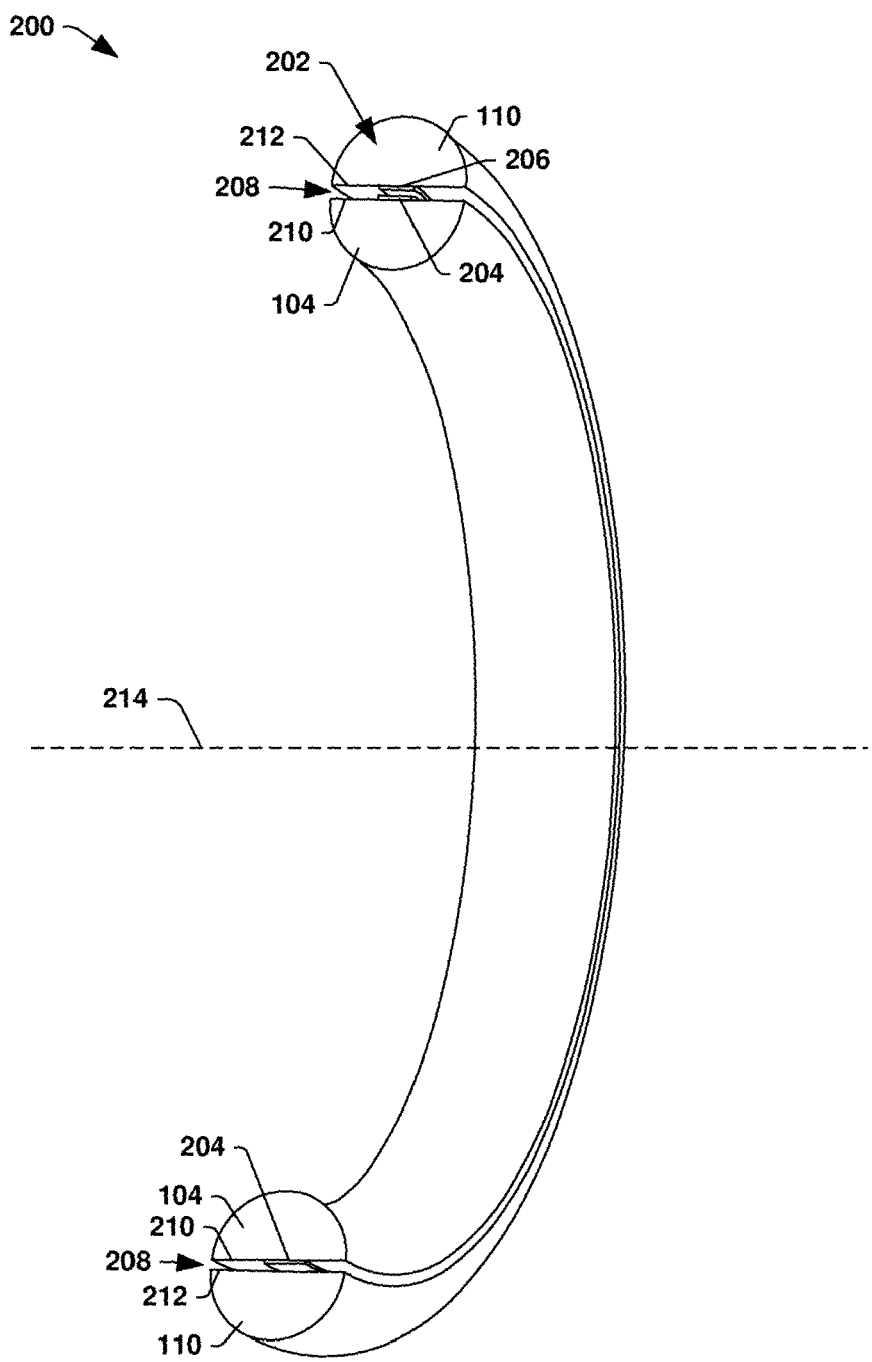
FIG. 2 illustrates an example rotor and stator, with a data communication system coupled to the rotor and the stator.

FIG. 2 illustrates a cross-sectional view 200 (e.g., taken along line 2-2 in FIG. 1) of a data communication system 202. The data communication system 202 comprises a transmitting antenna 204 and a receiving antenna 206 that are configured to be mounted to the rotor 104 and/or the stator 110. As illustrated herein, the rotor 104 and the stator 110 are respectively half circles separated from one another via an airgap 208. The airgap 208 enables rotation of the rotor 104 relative to the stator 110. As described herein, data can be wirelessly transmitted between the rotor 104 and the stator 110. In this way, data can be supplied to and/or from components comprised within the rotor 104, such as the radiation source(s) 118, the detector array 106, etc.

The transmitting antenna 204 can be mounted to a radial surface of the rotor 104 or the stator 110. For example, the transmitting antenna 204 can be coupled to an exterior radial surface 210 of the rotor 104. In another embodiment, the transmitting antenna 204 can be coupled to an interior radial surface 212 of the stator 110. In the illustrated example, the transmitting antenna 204 can extend substantially continuously around the exterior radial surface 210 of the rotor 104 or around the entire interior radial surface 212 of the stator 110. As such, the transmitting antenna 204 can form a nearly complete ring.

The receiving antenna 206 can be mounted to a radial surface of the rotor 104 or the stator 110. For example, the receiving antenna 206 can be coupled to the interior radial surface 212 of the stator 110 when the transmitting antenna 204 is coupled to the exterior radial surface 210 of the rotor 104. In another example, the receiving antenna 206 can be coupled to the exterior radial surface 210 of the rotor 104 when the transmitting antenna 204 is coupled to the interior radial surface 212 of the stator 110. In these examples, the receiving antenna 206 can face the transmitting antenna 204 such that data can be transmitted from the transmitting antenna 204, through the airgap 208, and to the receiving antenna 206.

In some examples, the receiving antenna 206 may not extend along the entire surface of the rotor 104 and/or the stator 110. Rather, the receiving antenna 206 can be coupled to a small portion of the rotor 104 and/or the stator 110. In the illustrated example, the receiving antenna 206 is coupled to the stator 110 and extends along the interior radial surface 212 of the stator 110 at an upper portion of the stator 110 but not along the interior radial surface 212 of the stator at a lower portion of the stator 110. In this way, as the rotor 104 rotates (e.g., about a rotational axis 214), a portion of the transmitting antenna 204 remains in close spatial proximity to the receiving antenna 206 allowing for data communication between the rotor 104 and the stator 110.

Figure 3A:
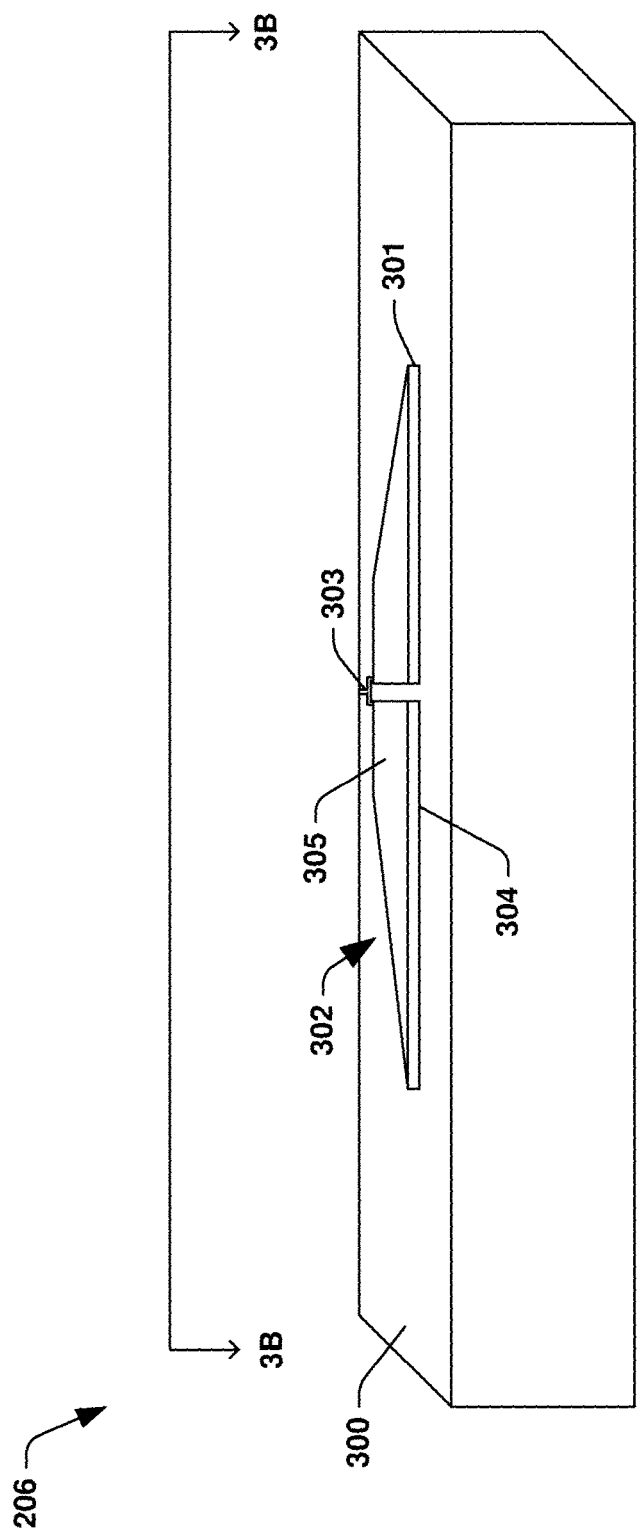
FIG. 3A illustrates a perspective view of an example receiving antenna comprising a conductive portion coupled to a dielectric portion.

FIG. 3A illustrates an example receiving antenna 206. The receiving antenna 206 can comprise a dielectric portion 300 and a conductive portion 302. In some embodiments, the receiving antenna 206 is constructed as a printed circuit board (PCB) with the conductive portion 302 comprising a conductive track or pad 301 and a conductive trace 303, which transmits an analog signal generated by the receiving antenna 206 to an analog-to-digital converter (e.g., ADC) or other electronic circuitry. The dielectric portion 300 can comprise any number of materials that are electrically insulating and are resistant to the flow of electric current therethrough. The dielectric portion 300 can comprise, for example, one or more of fiberglass, silicon, silicon dioxide, aluminum oxide, sapphire, germanium, gallium arsenide, etc.

The conductive portion 302 can comprise an electrically conductive material through which electric current is capable of being transmitted, such as copper, aluminum, etc. The conductive portion 302 can comprise a first surface 304, which is coupled to the dielectric portion 300, and a second surface 305, which faces away from the dielectric portion 300. By being coupled to the dielectric portion 300, the conductive portion 302 can be formed within, formed upon, attached to, etc., the dielectric portion 300.

Figure 3B:
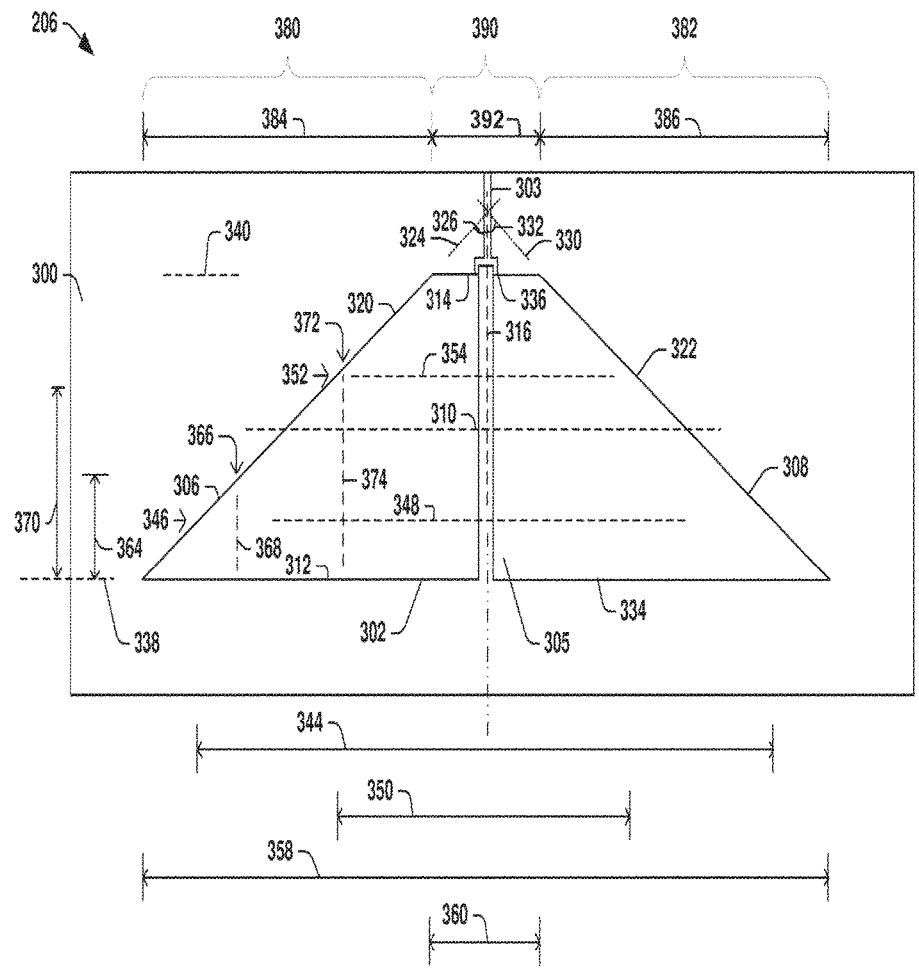
FIG. 3B illustrates a top down view of an example receiving antenna comprising a conductive portion coupled to a dielectric portion.

Turning to FIG. 3B, a top down view of the receiving antenna 206 as viewed from the perspective indicated by 3B-3B in FIG. 3A is illustrated. In the illustrated example, the conductive portion 302, or the conductive track/pad 301 thereof, may comprise a non-equiangular quadrilateral (e.g., rectangle, square, etc.) shape. That is, in an example, the conductive portion 302 may comprise a quadrilateral shape having unequal internal angles, such as by comprising a trapezoidal shape, an isosceles trapezoid shape, a parallelogram shape, etc. It will be appreciated that the conductive portion 302 is not limited to the shapes, configurations, dimensions, etc., illustrated herein.

The conductive portion 302 can extend between a first end 306 and a second end 308 along a conductive axis 310. In an example, the conductive axis 310 is substantially perpendicular to the rotational axis 214 (e.g., as illustrated in FIG. 2) about which the rotor 104 rotates. The conductive portion 302 can extend between a third end 312 and a fourth end 314 along a second conductive axis 316. In this example, the second conductive axis 316 is substantially perpendicular to the conductive axis 310. In an example, the second conductive axis 316 is substantially parallel to the rotational axis 214 about which the rotor 104 rotates.

The conductive portion 302 comprises a first wall 320 and a second wall 322. The first wall 320 defines the first end 306 of the conductive portion 302, and can extend between the first surface 304 (e.g., illustrated in FIG. 3A) and the second surface 305 of the conductive portion 302. In this example, the first wall 320 can extend linearly along a first wall axis 324 between the third end 312 and the fourth end 314 of the conductive portion 302. The first wall axis 324 can form an angle 326 with respect to the second conductive axis 316. In some examples, the angle 326 is between about 10 degrees to about 75 degrees.

The second wall 322 defines the second end 308 of the conductive portion 302, and can extend between the first surface 304 (e.g., illustrated in FIG. 3A) and the second surface 305 of the conductive portion 302. In this example, the second wall 322 can extend linearly along a second wall axis 330 between the third end 312 and the fourth end 314 of the conductive portion 302. The second wall axis 330 can form a second angle 332 with respect to the second conductive axis 316. In some examples, the second angle 332 is between about 10 degrees to about 75 degrees. In an example, the angle 326 and the second angle 332 are substantially equal. In this example, the first wall 320 of the conductive portion 302 is not parallel with respect to the second wall 322.

The conductive portion 302 comprises a third wall 334 and a fourth wall 336. The third wall 334 defines the third end 312 of the conductive portion 302, and can extend between the first surface 304 (e.g., illustrated in FIG. 3A) and the second surface 305 of the conductive portion 302. In this example, the third wall 334 can extend linearly along a third wall axis 338. The fourth wall 336 defines the fourth end 314 of the conductive portion 302. The fourth wall 336 can extend between the first surface 304 (e.g., illustrated in FIG. 3A) and the second surface 305 of the conductive portion 302. In this example, the fourth wall 336 can extend linearly along a fourth wall axis 340. In an example, the third wall 334, extending along the third wall axis 338, can be substantially parallel to the fourth wall 336, extending along the fourth wall axis 340. In this example, the third wall 334 may not form a right angle with respect to the first wall 320 and/or the second wall 322. In this example, the fourth wall 336 may not form a right angle with respect to the first wall 320 and/or the second wall 322.

The second surface 305 of the conductive portion 302 can have a non-constant, varying length along the second conductive axis 316 as measured between the first end 306 and the second end 308. For example, the second surface 305 can have a first length 344 at a first length location 346 along a first length axis 348 that is substantially parallel to the conductive axis 310. The second surface 305 can have a second length 350 at a second length location 352 along a second length axis 354 that is substantially parallel to the conductive axis 310 and the first length axis 348. In this example, the first length 344 is different than the second length 350. For example, the first length 344 is greater than the second length 350.

It will be appreciated that the illustrated locations of the first length location 346 and the second length location 352 are not intended to be limiting. Rather, the locations chosen with respect to FIG. 3B are merely intended to illustrate that at different locations along the second conductive axis 316, the length of the second surface 305 of the conductive portion 302 (e.g., as measured between the first end 306 and the second end 308) can vary. In the illustrated example, the first length location 346 can be located in closer proximity to the third end 312 than the second length location 352.

In an example, the third end 312 of the conductive portion 302 can have a third end length 358 measured between the first end 306 and the second end 308 along the third wall axis 338. The fourth end 314 of the conductive portion 302 can have a fourth end length 360 measured between the first end 306 and the second end 308 along the fourth wall axis 340. In this example, the third end length 358 is different than the fourth end length 360. For example, the third end length 358 can be greater than the fourth end length 360. In another example, the third end length 358 can be at least twice as long as the fourth end length 360.

The second surface 305 of the conductive portion 302 can have a non-constant, varying width along the conductive axis 310. For example, the second surface 305 can have a first width 364 at a first width location 366 along a first width axis 368 that is substantially parallel to the second conductive axis 316. In this example, the second surface 305 can have a second width 370 at a second width location 372 along a second width axis 374 that is substantially parallel to the second conductive axis 316 and to the first width axis 368. In this example, the first width 364 is different than the second width 370. For example, the first width 364 can be less than the second width 370.

It will be appreciated that the illustrated locations of the first width location 366 and the second width location 372 are not intended to be limiting. Rather, the locations chosen with respect to FIG. 3B are merely intended to illustrate that, at different locations along the conductive axis 310, the width of the second surface 305 of the conductive portion 302 can vary.

In the illustrated example of FIG. 3B, the conductive portion 302 may be asymmetric about the conductive axis 310. That is, a lower half of the conductive portion 302 (e.g., comprising the third end 312) may be asymmetric with respect to an upper half of the conductive portion 302 (e.g., comprising the fourth end 314). In this example, the conductive portion 302 may be symmetric about the second conductive axis 316. That is, a lateral half (e.g., a left half) of the conductive portion 302 (e.g., comprising the first end 306) may be symmetric with respect to an opposing lateral half (e.g., a right half) of the conductive portion 302 (e.g., comprising the second end 308).

The conductive portion 302 may comprise a first tapered portion 380 located at the first end 306 and a second tapered portion 382 located at the second end 308. In an example, the first tapered portion 380 can have a first tapered length 384 that is between about 6.35 millimeters (about 0.25 inch) to about 19 millimeters (about 0.75 inch). The first tapered length 384 can be measured between an end of the third wall 334 and a nearest end of the fourth wall 336. In an example, the second tapered portion 382 can have a second tapered length 386 that is between about 6.35 millimeters (about 0.25 inch) to about 19 millimeters (about 0.75 inch). The second tapered length 386 can be measured between an end of the third wall 334 and a nearest end of the fourth wall 336. In this example, by being tapered, the first tapered portion and/or the second tapered portion 382 can have non-constant widths as measured along the conductive axis 310.

A non-tapered portion 390 may be located between the first tapered portion 380 and the second tapered portion 382. In an example, the non-tapered portion 390 can have a non-tapered length 392 (e.g., corresponding to the fourth end length 360) that is between about 6.35 millimeters (about 0.25 inch) to about 100 millimeters (about 4 inches). By being non-tapered, the non-tapered portion 390 can have a substantially constant width as measured between the third end 312 and the fourth end 314. In a possible example, the non-tapered length (e.g., corresponding to the fourth end length 360) can be about 50 millimeters (about 2 inches) while the first tapered length 384 can be about 12.7 millimeters (about 0.5 inch) and the second tapered length 386 can be about 50 millimeters (about 2 inches). These dimensions can be chosen so as to increase the ability of the different frequencies of signals to reflect within the conductive portion 302 at different locations. As such, the likelihood of reflections of signals having a period that is an integer multiplier is reduced.

The size and shape of the conductive portion 302 allows for the receiving antenna 206 to receive signals at a higher frequency while allowing for the conductive portion 302 to have a longer length (e.g., corresponding to the third end length 358). This longer length of the conductive portion 302 can accommodate for annular gaps in the transmitting antenna 204. In an example, by having a tapered shape or a shape in which the conductive portion 302 has various lengths at different locations, the period associated with reflections of a signal can be different. In an example, a signal at a first frequency can travel within the conductive portion 302 and be reflected at the first length location 346 and the second length location 352. Due to the geometry of the conductive portion 302, a period of the reflection at the first length location 346 may be different than a period of the reflection at the second length location 352. Provided a length of the conductive portion 302 as measured at the first length axis 348 is not an integer multiplier of a length of the conductive portion 302 as measured at the second length axis 354, the period of the reflection at the first length location 346 will not be an integer multiplier of the period of the reflection at the second length location 352. The signal(s) can be transmitted to processing electronics (e.g., operational amplifiers, etc.) that are in electrical communication with the conductive portion 302 of the receiving antenna 206.

Figure 4:
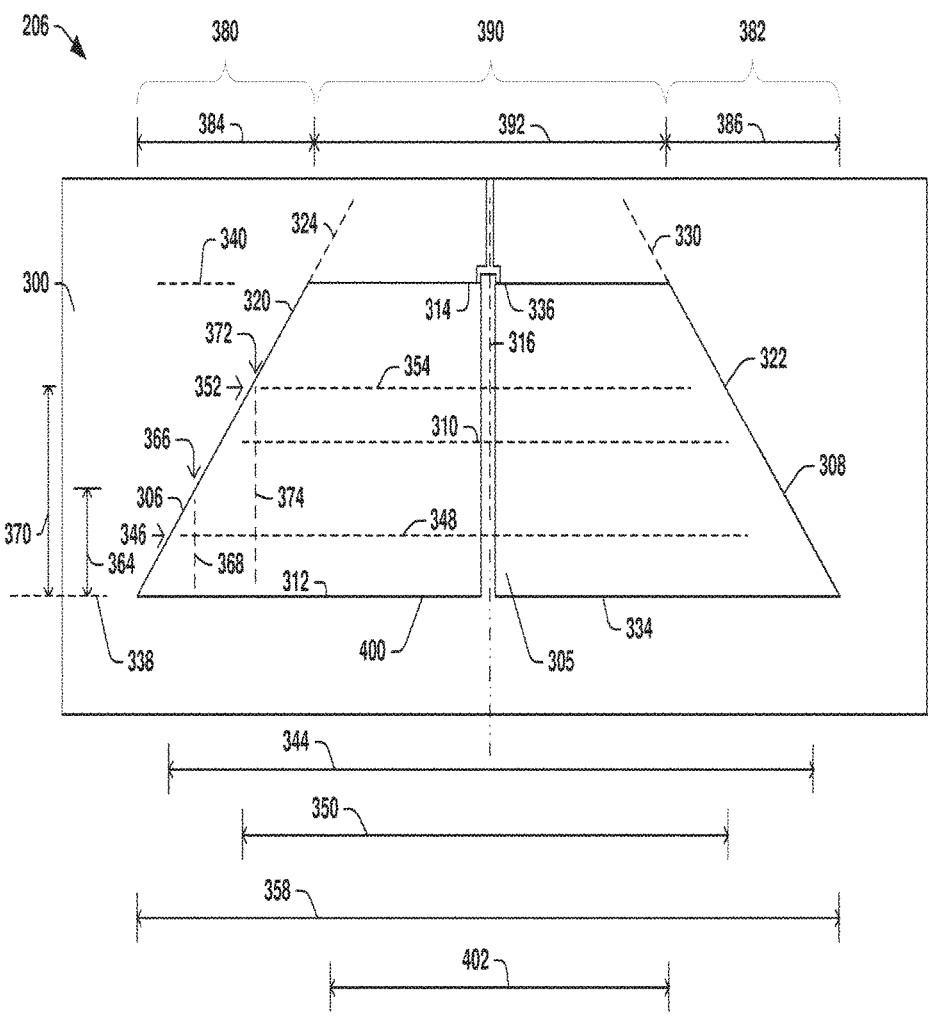
FIG. 4 illustrates a top down view of an example receiving antenna comprising a conductive portion coupled to a dielectric portion.

Turning to FIG. 4, a second example conductive portion 400 is illustrated. In this example, the fourth end 314 of the conductive portion 400 has a fourth end length 402 that is greater than the fourth end length 360 of the conductive portion 302 illustrated in FIG. 3B. In such an example, the angle between the first wall axis 324 and the second conductive axis 316 is less than the angle 326 illustrated in FIG. 3B. Similarly, in this example, the angle between the second wall axis 330 and the second conductive axis 316 is less than the angle 326 illustrated in FIG. 3B. In the example of FIG. 4, the first wall 320 of the conductive portion 400 can have a shorter length than the first wall 320 of the conductive portion 302 of FIG. 3B, and the second wall 322 of the conductive portion 400 can have a shorter length than the second wall 322 of the conductive portion 302 of FIG. 3B. As with the example illustrated in FIG. 3B, the conductive portion 400 may be asymmetric about the conductive axis 310. The conductive portion 400 may be symmetric about the second conductive axis 316. As with the example of FIG. 3B, the conductive portion 400 may comprise the first tapered portion 380 and the second tapered portion 382.

Figure 5:
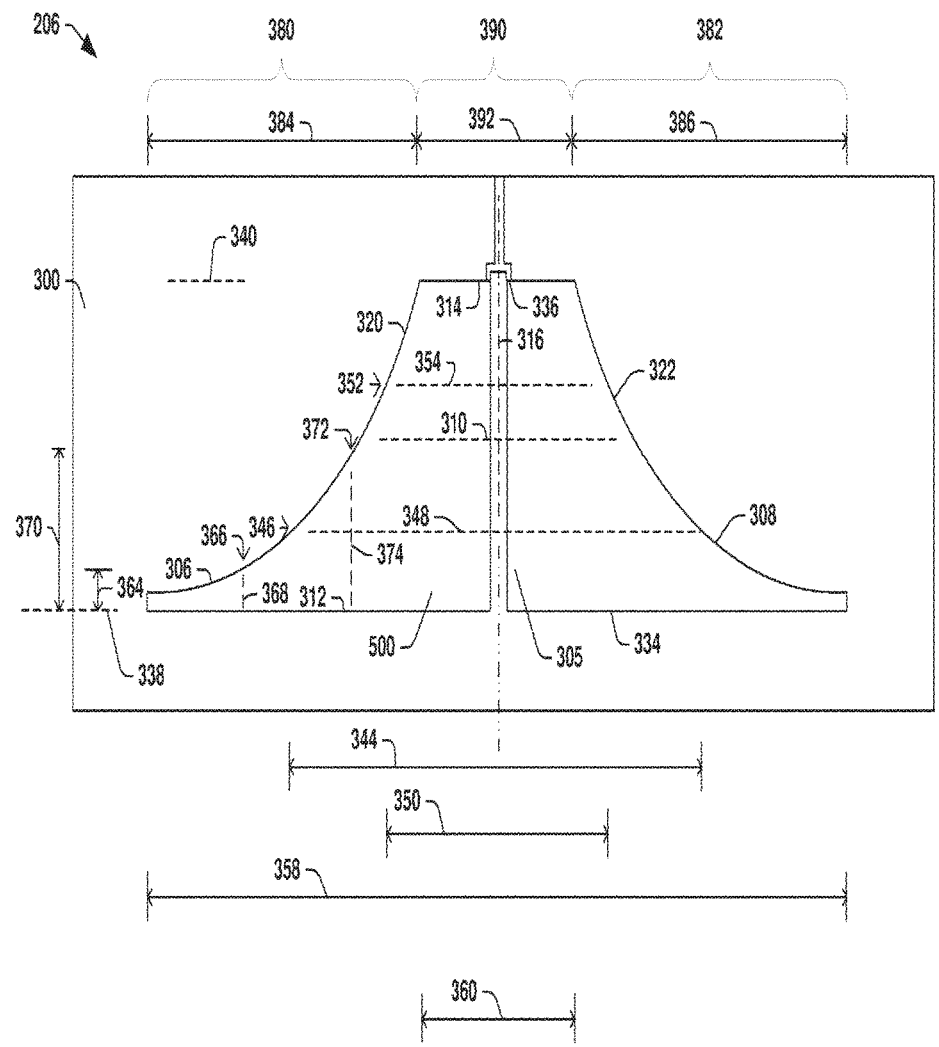
FIG. 5 illustrates a top down view of an example receiving antenna comprising a conductive portion coupled to a dielectric portion.

Turning to FIG. 5, a third example conductive portion 500 is illustrated. In this example, the first wall 320 and/or the second wall 322 of the conductive portion 500 can extend non-linearly. For example, the first wall 320 can extend non-linearly between the third end 312 and the fourth end 314 of the conductive portion 500. In the illustrated example, the first wall 320 and the second wall 322 are concave and bent inwardly toward a center of the conductive portion 500. In this example, the conductive portion 500 may be asymmetric about the conductive axis 310. The conductive portion 500 may be symmetric about the second conductive axis 316. As with the example of FIG. 3B, the conductive portion 500 may comprise the first tapered portion 380 and the second tapered portion 382.

Figure 6:
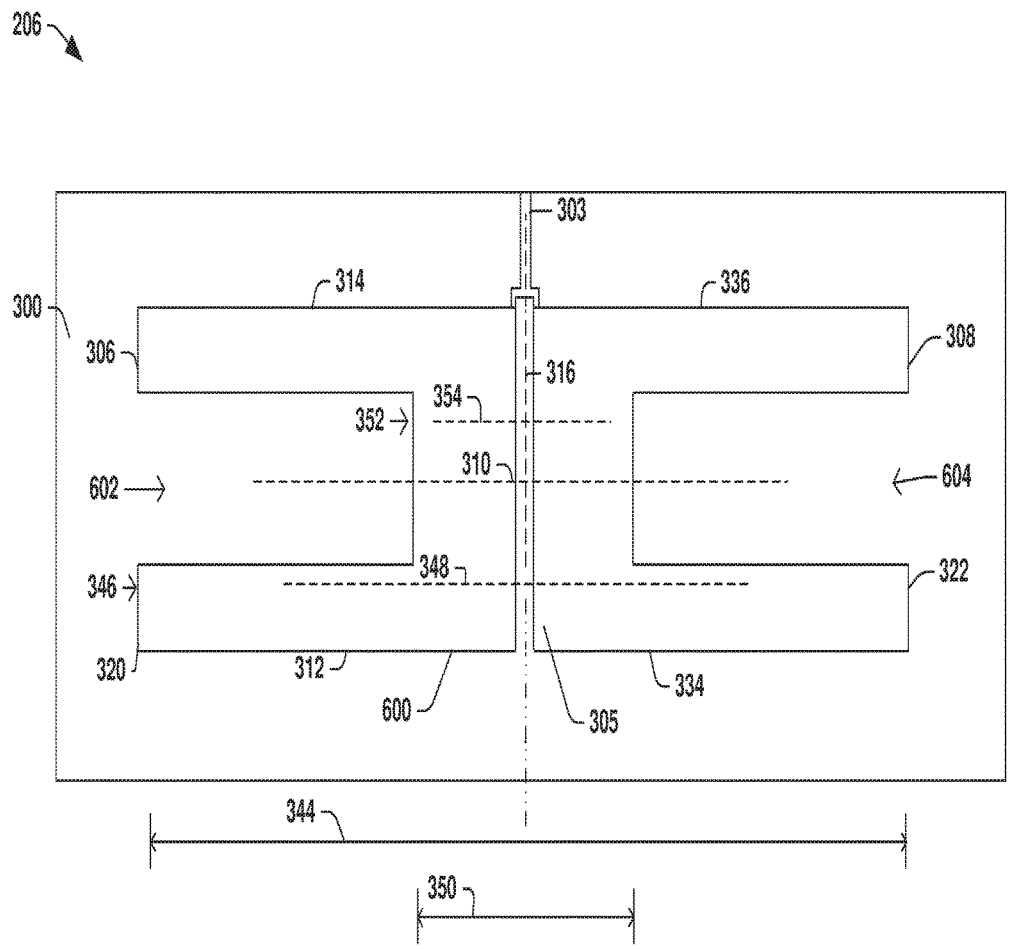
FIG. 6 illustrates a top down view of an example receiving antenna comprising a conductive portion coupled to a dielectric portion.

Turning to FIG. 6, a fourth example conductive portion 600 is illustrated. In this example, the first wall 320 and/or the second wall 322 of the conductive portion 600 can extend non-linearly between the third end 312 and the fourth end 314. In the illustrated example, a central portion of the first wall 320 extends inwardly toward a center of the conductive portion 600 to define a first recess 602 between the third end 312 and the fourth end 314. A central portion of the second wall 322 can extend inwardly toward a center of the conductive portion 600 to define a second recess 604 between the third end 312 and the fourth end 314. In an example, the conductive portion 600 can have an "H" shape, though other similar shapes are envisioned.

In this example, a central portion of the conductive portion 600 that is located between the third end 312 and the fourth end 314 along the second conductive axis 316 can have a central length (e.g., corresponding to the second length 350 at the second length location 352). The central length may be different than the length of the third end 312 or the fourth end 314 (e.g., corresponding to the first length 344 at a first length location 346). In this example, the central length of the conductive portion 600 can be less than the length of the third end 312 or the fourth end 314. In this example, the conductive portion 600 may be symmetric about the conductive axis 310. Likewise, in this example, the conductive portion 600 may be symmetric about the second conductive axis 316. As with the examples of FIGS. 3B, 4 and 5, the non-linear first wall 320 (e.g., defining the first recess 602) and the non-linear second wall 322 (e.g., defining the second recess 604) can allow for signals to reflect within the conductive portion 600, wherein the periods of the reflections may differ based upon the location along the non-linear walls 320, 322.

The words "example" and/or "exemplary" are used herein to mean serving as an example, instance, or illustration. Any aspect, design, etc., described herein as "example" and/or "exemplary" is not necessarily to be construed as advantageous over other aspects, designs, etc. Rather, use of these terms is intended to present concepts in a concrete fashion. As used in this application, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims may generally be construed to mean "one or more" unless specified otherwise or clear from context to be directed to a singular form. Also, at least one of A and B or the like generally means A or B or both A and B.

Although the disclosure has been shown and described with respect to one or more implementations, equivalent alterations and modifications will occur to others skilled in the art based upon a reading and understanding of this specification and the accompanying drawings. The disclosure includes all such modifications and alterations and is limited only by the scope of the claims. In particular regard to the various functions performed by the above described components (e.g., elements, resources, etc.), the terms used to describe such components are intended to correspond, unless otherwise indicated, to any component which performs the specified function of the described component (e.g., that is functionally equivalent), even though not structurally equivalent to the disclosed structure which performs the function in the herein illustrated example implementations of the disclosure. Similarly, illustrated ordering(s) of acts is not meant to be limiting, such that different orderings comprising the same or different (e.g., numbers) of acts are intended to fall within the scope of the present disclosure. In addition, while a particular feature of the disclosure may have been disclosed with respect to only one of several implementations, such feature may be combined with one or more other features of the other implementations as may be desired and advantageous for any given or particular application. Furthermore, to the extent that the terms "includes," "having," "has," "with," or variants thereof are used in either the Detailed Description or the claims, such terms are intended to be inclusive in a manner similar to the term "comprising."

What is claimed is:

1. A receiving antenna for wirelessly receiving data between a stator of a computed tomography (CT) imaging modality and a rotor of the CT imaging modality, the rotor configured to rotate about a rotational axis, the receiving antenna comprising:
    a dielectric portion; and
    a conductive portion having a first surface facing the dielectric portion and a second surface diametrically opposite the first surface, the conductive portion comprising:

a conductive trace;
a first section coupled to the conductive trace, the first section having at least a first wall and a second wall; and
a second section spaced apart from the first section and coupled to the conductive trace, the second section having at least a first wall and a second wall; wherein:
the second wall of the first section is parallel to the second wall of the second section,
the first wall of the first section is disposed on a diametrically opposite side of the first section relative to the second section, and
the first section is tapered such that a first distance between the first wall of the first section and the second wall of the first section at a first location along the second wall of the first section is different than a second distance between the first wall of the first section and the second wall of the first section at a second location along the second wall of the first section.

2. The receiving antenna of claim 1, wherein:
the conductive trace contacts the second wall of the first section;
the second wall extends between the first wall and a third wall of the first section;
the first wall is not perpendicular to the second wall of the first section; and
the third wall is perpendicular to the second wall of the first section.

3. The receiving antenna of claim 2, wherein:
a fourth wall extends between the first wall and the third wall of the first section;
the first wall is not perpendicular to the fourth wall of the first section; and
the fourth wall is perpendicular to the third wall of the first section.

4. The receiving antenna of claim 1, wherein the conductive portion is symmetric about an axis parallel to the second wall of the first section.

5. The receiving antenna of claim 3, wherein the fourth wall is parallel to the second wall of the first section.

6. The receiving antenna of claim 2, wherein:
the first section comprises a fourth wall extending between the first wall and the third wall of the first section;
a length of the first section, measured between the first wall and the third wall in a direction parallel to the second surface and perpendicular to the first axis, decreases linearly in a direction from the fourth wall to the second wall.

7. The receiving antenna of claim 2, wherein:
the first section comprises a fourth wall disposed diametrically opposite the second wall,
a length of the first section, measured between the first wall and the third wall in a direction parallel to the second surface and perpendicular to the first axis, decreases non-linearly in a direction from the fourth wall to the second wall.

8. The receiving antenna of claim 7, wherein the conductive portion is symmetric about an axis parallel to the second wall of the first section.

9. The receiving antenna of claim 6, wherein the conductive portion is symmetric about an axis parallel to the second wall of the first section.

10. A receiving antenna for wirelessly receiving data between a stator of a computed tomography (CT) imaging modality and a rotor of the CT imaging modality, the rotor configured to rotate about a rotational axis, the receiving antenna comprising:
a dielectric portion; and
a conductive portion comprising a first surface facing the dielectric portion and a second surface diametrically opposite the first surface, wherein:
the conductive portion extends between a first end and a second end in a direction substantially parallel to the rotational axis,
a first wall defines a third end of the conductive portion, the first wall extending linearly between the first end and the second end of the conductive portion; and
the second surface of the conductive portion has:
a first width at a first width location along a first width axis that is substantially parallel to the rotational axis; and
a second width at a second width location along a second width axis that is substantially parallel to the rotational axis, wherein the first width is different than the second width.

11. The receiving antenna of claim 10, wherein the first width is less than the second width.

12. The receiving antenna of claim 10, wherein the first wall extends linearly along a first wall axis between the first end and the second end of the conductive portion, the first wall axis at an angle with respect to the rotational axis that is between about 15 degrees to about 75 degrees.

13. A computed tomography (CT) imaging modality comprising:
a stator;
a rotor configured to rotate relative to the stator about a rotational axis; and
a receiving antenna coupled to the stator or the rotor for wirelessly receiving data between the stator and the rotor, the receiving antenna comprising:
a dielectric portion; and
a conductive portion having a first surface facing the dielectric portion and a second surface diametrically opposite the first surface, the conductive portion comprising:
a conductive trace;
a first section coupled to the conductive trace, the first section having at least a first wall and a second wall; and
a second section spaced apart from the first section and coupled to the conductive trace, the second section having at least a first wall and a second wall; wherein:
the second wall of the first section is parallel to the second wall of the second section,
the first wall of the first section is disposed on a diametrically opposite side of the first section relative to the second section, and
the first section is tapered such that a first distance between the first wall of the first section and the second wall of the first section at a first location along the second wall of the first section is different than a second distance between the first wall of the first section and the second wall of the first section at a second location along the second wall of the first section.

14. The CT imaging modality of claim 13, wherein:
the conductive trace contacts the second wall of the first section;
the second wall extends between the first wall and a third wall of the first section;

the first wall is not perpendicular to the second wall of the first section; and the third wall is perpendicular to the second wall of the first section.

15. The CT imaging modality of claim 14, wherein the conductive portion is symmetric about an axis parallel to the second wall of the first section.

\* \* \* \* \*